United States Patent [19]

Thomson et al.

[11] Patent Number: 4,661,524
[45] Date of Patent: Apr. 28, 1987

[54] TOPICAL TREATMENT AND COMPOSITION

[75] Inventors: Michael J. Thomson, Harlow; Frank R. Mangan, Bishops Stortford, both of England

[73] Assignee: Beecham Group P.L.C., Brentford, England

[21] Appl. No.: 814,205

[22] Filed: Dec. 27, 1985

Related U.S. Application Data

[63] Continuation-in-part of Ser. No. 750,037, Jun. 28, 1985, abandoned.

[30] Foreign Application Priority Data

Jun. 29, 1984 [GB] United Kingdom ............. 8416638

[51] Int. Cl.$^4$ .................. A61K 31/12; A61K 31/045
[52] U.S. Cl. .................................. 514/682; 514/730
[58] Field of Search ............................. 514/682, 730

[56] References Cited

U.S. PATENT DOCUMENTS 4,126,681 11/1978 Reller ................................. 514/160
4,514,386 4/1985 Yamashira et al. ............. 514/420

FOREIGN PATENT DOCUMENTS 0003074 4/1981 European Pat. Off.
0003643 9/1982 European Pat. Off.

OTHER PUBLICATIONS

E. A. Boyle et al., "Nabumetone (BRL 14777, 4-[6-Methoxy-2-Naphthyl]-Butan-2-One): A New Anti-Inflammatory Agent," *J. Pharm. Pharmacol.*, 34, pp. 562–569 (1982).

G. B. Fregnan and A. L. Torsello, "Topical Anti-Inflammatory Activity of Dexamethasone 17-Valerate and Other Corticosteroids", *Current Therapeutic Research*, 17, pp. 375–381 (1975).

R. E. Haddock et al., "Metabolism of Nabumetone (BRL 14777) by Various Species Including Man", *Xenobiotica*, 14, pp. 327–337 (1984).

*Primary Examiner*—Stanley J. Friedman
*Attorney, Agent, or Firm*—Charles B. Smith; James F. Haley, Jr.; Irene J. Frangos

[57] ABSTRACT

Pharmaceutical compositions with comprise a compound of the formula (I):

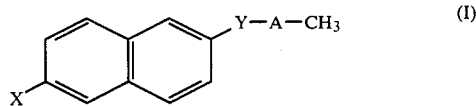

wherein X is a chlorine or bromine atom or a methoxyl, methylthio or alkyl group of 1–4 carbon atoms; Y is a —$CHR_1$—$CH_2$— or —$CR_1$=CH— group where $R_1$ is a hydrogen atom or a methyl group and A is a CHOH or CO group, and a pharmaceutically acceptable carrier selected from the group of creams, ointments, lotions, gels, aerosols, sprays, liniments and gel sticks. The compositions possess systemic anti-inflammatory activity when administered topically.

16 Claims, No Drawings

TOPICAL TREATMENT AND COMPOSITION

This is a continuation-in-part of application Ser. No. 750,037, filed June 28, 1985, entitled Topical Treatment And Composition, now abandoned.

This invention relates to pharmaceutical compositions and methods for the treatment of inflammation by topical administration of compounds having anti-inflammatory activity.

United Kingdom Patent No. 1,474,377 refers to pharmaceutical compositions which comprise a compound of the formula (I):

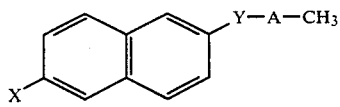

wherein X is a chlorine or bromine atom or a methoxyl, methylthio or alkyl group of 1-4 carbon atoms; Y is a —CHR$_1$—CH$_2$— or —CR$_1$=CH— group where R$_1$ is a hydrogen atom or a methyl group and A is a CHOH or CO group, and a pharmaceutically acceptable carrier, and its use in the treatment of inflammation. The '377 patent refers only to oral administration of the compound of formula (I), and specifically mentions only tablets or capsules.

We have now found that the compounds of the formula (I) unexpectedly possess local topical anti-inflammatory activity, and possess systemic anti-inflammatory activity when administered topically.

Accordingly, the present invention relates to the use of a compound of the formula (I) for the manufacture of a medicament for the treatment or prophylaxis of inflammation by topical administration to mammals, including humans and to anti-inflammatory pharmaceutical compositions for topical administration comprising compounds of the formula (I).

In this description, the following terms are employed:

Aerosol—Pharmaceutical aerosols are products that are packaged under pressure and contain therapeutically active ingredients that are released upon activation of an appropriate valve system. The term "aerosol" has been used to refer to the fine mist of spray that is emitted from a pressurized container containing an active ingredient and a propellant. However, the term has been broadly applied to include all self-contained pressurized products, some of which deliver foams or semisolid fluids. Accordingly, unless indicated otherwise, a reference herein to an aerosal formulation of the present invention should be understood to include pharmaceutical compositions for topical use comprising a compound of the formula I and a pharmaceutically acceptable carrier which includes a propellant, said compositions being adapted for use in a pressurized container that dispenses the composition as a spray, foam or semisolid liquid.

An aerosol generally comprises a container, a propellant, a concentrate containing the active ingredient, a valve (which may be a metered valve), and an actuator. The nature of these components determines characteristics such as delivery rate, foam density, and fluid viscosity. Aerosols may be two-phase (gas and liquid) or three-phase (gas, liquid, and solid or liquid) formulations. A two-phase formulation consists of a solution of active ingredients in liquified propellant and the vaporized propellant. The solvent may be the propellant or a mixture of the propellant and co-solvents such as alcohol, propylene glycol, and polyethylene glycols which are often used to enhance the solubility of the active ingredients. Three-phase formulations consist of a suspension or emulsion of the active ingredient(s) in addition to the vaporized propellants. A suspension consists of the active ingredient(s) dispersed in the propellant system with the aid of suitable excipients such as wetting agents and/or solid carriers such as talc or colloidal silicas. A foam formulation is generally an emulsion containing one or more active ingredients, surfactants, aqueous or nonaqueous liquids, and the propellants. If the propellant is in the internal (discontinuous) phase (i.e., of the oil-in-water type), a stable foam is discharged, and if the propellant is in the external (continuous) phase (i.e., of the water-in-oil type), a spray or a quick-breaking foam is discharged. [See *The United States Pharmacopeia*, XXI ("USP") at 1334].

Gel—Gels are semisolid systems consisting either of suspensions made up of small inorganic particles or of large organic molecules interpenetrated by a liquid. Where the gel consists of a network of small discrete particles, the gel is classified as a two-phase system. In a two-phase gel, if the particle size of the dispersed phase is relatively large, the gel is sometimes referred to as a magma. Both gels and magmas may be thixotropic, forming semisolids on standing and becoming liquid on agitation. They should be shaken before use to ensure homogeneity.

Single-phase gels consist of organic macromolecules uniformly distributed throughout a liquid so that no apparent boundaries exist between the dispersed macromolecules and the liquid. Single-phase gels may be made from synthetic macromolecules (e.g. Carbomer)* or from natural gums (e.g., *Tragacanth*). The latter preparations are also called mucilages. Although single-phase gels are commonly aqueous, alcohols and oils may also be used as the continuous phase. For example, mineral oil can be combined with a polyethylene resin to form a gel which may be used as an oleaginous ointment base [see *USP, supra* at 1336].

* Formulations that are capitalized in this discussion are classified as pharmacopeial preparations (USP).

Ointment—Ointments are semisolid preparations which are intended for external application to the skin or mucous membranes. Ointment bases include hydrocarbon bases, absorption bases, water-removable bases, and water-soluble bases.

Hydrocarbon bases, also known as oleaginous ointment bases include *White Petrolatum* and *White Ointment*. Only small amounts of an aqueous component can be incorporated into these bases. They serve to keep medicaments in prolonged contact with the skin and act as occlusive dressings because they are difficult to wash off.

Absorption bases include (a) bases that permit the incorporation of aqueous solutions with the formation of a water-in-oil emulsion (e.g., *Hydrophilic Petrolatum* and *Anhydrous Lanolin*), and (b) water-in-oil emulsions that permit the incorporation of additional quantities of aqueous solutions (e.g., Lanolin and Cold Cream).

Water-removable bases are oil-in-water emulsions, e.g., *Hydrophilic Ointment,* and are frequently called "creams." They are also described as "water-washable," since they may be readily washed from the skin or clothing with water, which makes them more acceptable for cosmetic reasons. Some medicaments may be more effective in these bases than in hydrocarbon bases.

Water-soluble bases, also known as greaseless ointment bases, are composed of water-soluble constituents. Bases of this type possess many of the advantages of the water-removable bases and, in addition, contain no water-insoluble substances such as petrolatum, anhydrous lanolin, or waxes. An example of a water-soluble bases is *Polyethylene Glycol Ointment*, whose formula may be modified by the addition of stearyl alcohol where water, or a water solution, is to be incorporated in order to minimize the resultant softening effect. The water-soluble bases may in some instances be irritating to inflamed tissue [see *USP, supra* at 1337].

Lotion—Preferred lotions include fluid or thixotropic emulsions or suspensions intended for external application to the body. Some lotions consist of finely powdered, insoluble solids held in more or less permanent suspension by the presence of suspending agents and/or surface-active agents. Others are emulsions of the oil-in-water type stabilized by a surface-active agent. Both types of lotions may separate or stratify on long standing, and should be well shaken before each use. Adequate preservation against microbial contamination is required [see *USP, supra* at 1337].

Cream—As used in this description, creams are viscous, liquid or semisolid emulsions of either the oil-in-water or the water-in-oil type. They are to be used topically. The term "cream" is most frequently applied to soft, cosmetically acceptable types of preparations [see *USP, supra* at 1335].

Gel stick—The definition of gel sticks set forth in *Harry's Cosmeticology*, 6th Edition, at 740, is hereby incorporated herein by reference.

Liniment—Liniments are solutions or mixtures of various substances in oil, alcoholic solutions of soap, or emulsions. They are intended for external application and are usually applied with friction and rubbing of the skin, the oil or soap base providing for ease of application and massage. Alcoholic liniments generally penetrate the skin more readily than do those with an oil base [see *Remington's*, 16th Edition, at 1451].

Spray—As used in this description, spray formulations are solutions of various drugs which are applied topically from a container having a spray means (e.g., an atomizer or nebulizer). The vehicle is preferably aqueous but other pharmaceutically acceptable vehicles (e.g., alcohols such as ethanol) may also be used.

The present invention provides a method of treatment or prophylaxis of inflammation in mammals, including humans, comprising topical administration of an anti-inflammatory topically effective amount of a compound of the formula (I).

The compounds of formula (I) will be administered as a pharmaceutical composition for topical administration. Suitable formulations include creams, ointments, lotions, gels, sprays, aerosols, gel sticks, and liniments.

The compounds of formula (I) may be used in the topical treatment of atopic and contact dermatitis, psoriasis, eczema and other inflammatory dermatoses and in inflammatory conditions of eyes, ears, nose and throat.

They may also be used in the treatment by topical administration of osteo- and rheumatoid arthritis and sprains, strains, tendonitis and bursitis.

It will be appreciated that the topically effective amount of the compound of the formula (I) used will depend on a number of factors such as the nature and severity of the disorder being treated, and the specific compound being used. However, by way of illustration it is believed that effective therapy can be achieved using roughly similar amounts of the compounds of formula (I) as would be used of hydrocortisone. A typical formulation suitable for treating an adult human will suitably contain about 0.1% to about 10% by weight, more suitably about 0.5% to about 5% by weight of the compound of formula (I).

A topical pharmaceutical composition for the method of treatment of the present invention may be administered from 1 to 6 times daily, and more usually from 2 to 4 times daily.

The present invention also provides a topically effective anti-inflammatory pharmaceutical composition which comprises a topically effective amount of a compound of formula (I) together with a pharmaceutically acceptable carrier.

Creams, ointments, lotions, gels, sprays, aerosols, liniments or gel sticks that may be used for compounds of the formula (I) are conventional formulations well known in the art, for example, as described in standard text books of pharmaceutics and cosmetics, such as Harry's Cosmeticology published by Leonard Hill Books, the British Pharmacopoeia, Remington's Pharmaceutical Sciences, 16th Edition (1980), published by Mack Publishing Company (Easton, Pa.), and the United States Pharmacopeia, Twenty First Revision (USP XXI) (1984), distributed by Mack Publishing Company, the disclosures of these texts being hereby incorporated herein by reference. A standard emulsifying oil-in-water or water-in-oil vehicle or an anydrous polyethylene glycol base are examples of such suitable formulations.

Examples of oils suitable for inclusion in a standard emulsifying ointment base include mineral oils, vegetable oils, synthetic fatty acid esters, fatty alcohols, lanolin and its derivatives.

Many of the compositions of this invention will normally include a suitable emulsifier. The composition can range from liquid through semi-liquid to gel types according to the type of emulsion and quantity of any thickening agent which may be present. Examples of emulsifiers include polyhydric alcohol esters such as sorbitan monostearate, fatty acid esters such as glyceryl monostearate, and polyester derivatives of fatty acids or fatty alcohols.

The compositions may also contain antioxidants and other conventional ingredients such as preservatives, perfumes and alcohol. Advantageously, a penetrating agent such as 'Azone' may also be included.

The compositions of this invention may further contain other therapeutic agents such as anti-infective agents and/or anti-viral agents. Suitable anti-infective agents include the topically applicable antibacterial, anti-yeast and anti-fungal agents already in use in topical anti-inflammatory preparations. As anti-viral agents, there may be particularly mentioned anti-herpes agents (e.g., acyclovir).

In the compounds of formula (I) X is preferably methoxy, Y is preferably $CHR_1$—$CH_2$ where $R_1$ is a hydrogen atom, and A is preferably a CO group, so that a preferred compound of formula (I) for use in the treatment and compositions of the present invention is that of formula (II):

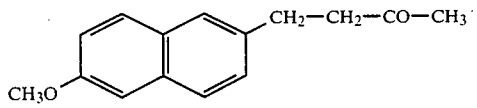

Further compounds of formula (I) are also referred to in United Kingdom Pat. No. 1,474,377.

The compounds of formulae (I) and (II) may be prepared as described in the '377 patent, or as described in European Pat. Nos. 0003374 or 0003643.

The following pharmacological data illustrate the efficacy of the compounds of formula (I) in the topical treatment or prophylaxis of inflammation.

PHARMACOLOGICAL DATA

The compound of formula (II) was tested for topical anti-inflammatory activity in an animal model based on that described by G. B. Fregnan and A. L. Torsello, *Current Therapeutical Research*, 17, No. 4, 375–381 (1975). In outline, the method is as follows:

Animals:
Rats, Charles River Wistar Strain, female, 9/group. Weight range 200–240 g.
Irritant:
Irritant solution applied consists of 1% croton oil in tetrahydrofuran.
Procedure:
We placed 0.05 ml of irritant solution on each ear, the compound under test being included in the irritant solution on one ear. Six hours later we removed the ears by cutting along the hairline. We then weighed the ears.
−ve controls—no irritant solution.
+ve controls—irritant solution on both ears.
Our results are as shown in Table 1, where the compound of formula (II) is denoted (II).

TABLE 1

| TREATMENT | DOSE (mg/ear) | INCREASE IN EAR WEIGHT MG ± S.E. | % INHIBITION |
| --- | --- | --- | --- |
| Vehicle | — | 68.4 ± 6.4*** | — |
| (II) | 4 | 27.9 ± 2.7 | 59 |

Significantly different from the control assessed by the Students 't' test.
***p < 0.001 9 rats/group Toxicity
No toxic effects were observed in the above test.
We claim:

1. A topically effective anti-inflammatory pharmaceutical composition which comprises a topically effective anti-inflammatory amount of a compound of the formula (I):

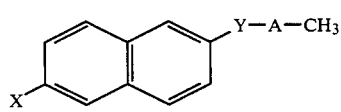

wherein X is a chlorine or bromine atom or a methoxyl, methylthio or alkyl group of 1–4 carbon atoms; Y is a —$CHR_1$—$CH_2$— or —$CR_1$=CH— group where $R_1$ is a hydrogen atom or a methyl group and A is a CHOH or CO group, and a pharmaceutically acceptable carrier, said composition being selected from the group consisting of creams, ointments, lotions, gels, aerosol formulations, spray formulations, liniments and gel sticks.

2. The composition according to claim 1 wherein the anti-inflammatory amount of the compound of formula (I) comprises from about 0.1% by weight to about 10% by weight of the total composition.

3. The composition according to claim 1 wherein the anti-inflammatory amount of the compound of formula (I) comprises from about 0.5% by weight to about 5% by weight of the total composition.

4. The composition according to claim 1 wherein the compound of formula (I) is 4-(6'-methoxy-2'-naphthyl)-butan-2-one.

5. The composition according to claim 1, wherein the composition is a cream.

6. The composition according to claim 1, wherein the composition is a ointment.

7. The composition according to claim 1, wherein the composition is a lotion.

8. The composition according to claim 1, wherein the composition is a gel.

9. The composition according to claim 1, wherein the composition is an aerosol.

10. The composition according to claim 1, wherein the composition is a gel stick.

11. The composition according to claim 1, wherein the composition is a liniment.

12. The composition according to claim 1, wherein the composition is a spray formulation.

13. A method for treatment or prophylaxis of inflammation in mammals comprising topically administering to a mammal an anti-inflammatory topically effective amount of a compound of formula (I)

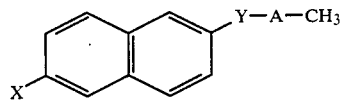

wherein X is a chlorine or bromine atom or a methoxyl, methylthio or alkyl group of 1–4 carbon atoms; Y is a —$CHR_1$—$CH_2$— or —$CR_1$=CH— group where $R_1$ is a hydrogen atom or a methyl group and A is a CHOH or CO group.

14. The method according to claim 3 wherein the compound of formula (I) is 4-(6'-methoxy-2'-naphthyl)-butan-2-one.

15. A spray container comprising a spray means and a spray formulation according to claim 1.

16. A pressurized spray container comprising an aerosol formulation according to claim 1.

* * * * *